United States Patent [19]

Wolfers et al.

[11] 4,369,329

[45] Jan. 18, 1983

[54] SUBSTITUTED TARTARIC ACID ESTERS, A PROCESS FOR THEIR PRODUCTION AND THEIR USE AS POLYMERIZATION INITIATORS

[75] Inventors: Heinrich Wolfers, Reurdt; Hans Rudolph, Krefeld; Heinrich Alberts, Cologne, all of Fed. Rep. of Germany

[73] Assignee: Bayer Aktiengesellschaft, Leverkusen, Fed. Rep. of Germany

[21] Appl. No.: 128,801

[22] Filed: Mar. 10, 1980

[30] Foreign Application Priority Data

Mar. 14, 1979 [DE] Fed. Rep. of Germany ....... 2909951

[51] Int. Cl.³ .......................... C07F 7/04; C07F 7/08; C07F 7/18
[52] U.S. Cl. ..................................... 556/442; 560/55; 560/61; 560/87; 560/127; 560/180
[58] Field of Search ................... 560/55, 180, 127, 61, 560/86; 556/442

[56] References Cited

U.S. PATENT DOCUMENTS

| | | | |
|---|---|---|---|
| 3,247,109 | 4/1966 | Benoit | 560/180 X |
| 3,816,318 | 6/1974 | Hentschel | 560/180 X |
| 3,965,170 | 6/1976 | Krause | 560/180 X |
| 3,965,171 | 6/1976 | Krause | 560/180 X |

*Primary Examiner*—Paul F. Shaver
*Attorney, Agent, or Firm*—Connolly and Hutz

[57] ABSTRACT

Ethers of 1,2-disubstituted tartaric acid esters proved to be excellent initiators for thermally initiatable radical polymerization reactions. They show a high reactivity even in low concentrations and yield thoroughly hardened products.

2 Claims, No Drawings

SUBSTITUTED TARTARIC ACID ESTERS, A PROCESS FOR THEIR PRODUCTION AND THEIR USE AS POLYMERIZATION INITIATORS

This invention relates to new substituted tartaric acid esters, to a process for their production from—ketocarboxylic acid esters and organohalogen compounds or halogen silanes and to their use as initiators for radically initiable polymerization reactions.

On account of the known dangers of polymerization initiators containing peroxide groups, 1,1,2,2-tetraaryl-1,2-dihydroxyethanes, their alkyl and silyl ethers have already been proposed as initiators for thermally initiatable radical polymerization reactions (German Auslegeschrifts Nos. 1,216,877 and 1,219,224, German Auslegeschrifts Nos. 2,131,623 and 2,164,482). Other known initiators include 1,2-diaryl-1,2-dicyano-1,2-dihalogen ethanes (German Offenlegungsschrift No. 2,444,252), 1,2-diaryl-1,1,2,2-tetracarbalkoxy ethanes (U.S. Patent No. 3,896,099) and 1,2-diaryl-1,1,2,2-tetramethyl ethanes containing partially chlorinated methyl groups (Belgian Patent No. 834,599). It is also known that silyl ethers of oligomers containing recurring units with the following structure:

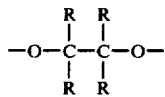
(I)

in which R represents phenyl or alkyl, can be used for initiating polymerization reactions, in some cases even at temperatures just above 40° C. (German Offenlegungsschrifts Nos. 2,632,294 and 2,656,782).

There is a need for peroxide-group-free initiators which are stable in storage at room temperature in the compounds or mixtures to be polymerized, show greater reactivity at elevated temperatures than the known peroxide-free initiators in as low a concentration as possible in the polymerizable system, and give thoroughly hardened products (as determined by measuring the residual styrene content).

It has now surprisingly been found that the ethers of substituted tartaric esters defined hereinafter satisfy these requirements. In addition, they have the advantage that, on decomposing into radicals, they do not release any volatile fractions which could give rise to undesirable bubble formation in the polymer.

Accordingly, the present invention provides ethers of 1,2-disubstituted tartaric acid esters corresponding to the following formula (II):

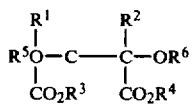
(II)

in which $R^1$ and $R^2$, which may be the same or different, represent linear or branched $C_1$-$C_{10}$ alkyl radicals optionally substituted by methoxy, chlorine or fluorine, preferably methyl, ethyl, isopropyl, t-butyl, isobutyl, n-butyl, hexyl or octyl; $C_5$-$C_7$ cycloalkyl radicals optionally substituted by $C_1$-$C_4$ alkyl, methoxy, chlorine or fluorine, preferably cyclopentyl or cyclohexyl; $C_7$-$C_{10}$ aralkyl radicals optionally substituted by $C_1$-$C_4$ alkyl, methoxy, chlorine or fluorine, preferably benzyl; $C_6$-$C_{12}$ aryl radicals optionally substituted by $C_1$-$C_4$ alkyl, methoxy, chlorine or fluorine, preferably phenyl, tolyl, chlorophenyl, dichlorophenyl, naphthyl, biphenylyl or t-butyl phenyl, $R^3$ and $R^4$, which may be the same or different, represent linear or branched $C_1$-$C_{18}$ alkyl radicals optionally substituted by methoxy, chlorine or fluorine, preferably methyl, ethyl, isopropyl, butyl, hexyl, octyl, lauryl or stearyl; $C_5$-$C_7$ cycloalkyl radicals optionally substituted by $C_1$-$C_4$ alkyl, methoxy, chlorine or fluorine, preferably cyclohexyl; $C_7$-$C_{10}$ aralkyl radicals optionally substituted by $C_1$-$C_4$ alkyl, methoxy, chlorine or fluorine, preferably benzyl or β-phenyl ethyl; $C_6$-$C_{10}$ aryl radicals optionally substituted by $C_1$-$C_4$ alkyl, methoxy, chlorine or fluorine, preferably phenyl, tolyl, chlorophenyl or naphthyl; or triorganosilyl radicals containing from 3 to 18 carbon atoms, preferably trimethyl silyl, triethyl silyl and triphenyl silyl, $R^5$ and $R^6$, which may be the same or different, represent (1) a hydrogen atom with the proviso that at most one of the two substituents is a hydrogen atom;

(2) $C_1$-$C_{10}$ alkyl radicals optionally substituted by methoxy, chlorine or fluorine, preferably methyl, ethyl, isopropyl, isobutyl, hexyl or octyl; $C_5$-$C_7$ cycloalkyl radicals optionally substituted by $C_1$-$C_4$ alkyl, methoxy, chlorine or fluorine, preferably cyclohexyl; $C_7$-$C_{10}$ aralkyl radicals optionally substituted by $C_1$-$C_4$ alkyl, methoxy, chlorine or fluorine, preferably benzyl or β-phenyl ethyl; or (3) $SiR^7R^8(O_nSiR^9R^{10})_mR^{11}$ and $R^7$, $R^8$, $R^{11}$, which may be the same or different, represent (a) methyl, ethyl, phenyl, benzyl, chloromethyl, hydroxyl, methoxy or ethoxy, or (b) a radical corresponding to the following formula:

(III)

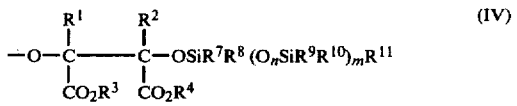
(IV)

$R^9$ and $R^{10}$, which may be the same or different, are as defined in (3a), and n=0 or 1, m=0 or an integer of from 1 to 10; in which the compounds of formula (II) in case (3) may contain the component structure:

(V)

attached through silicon atoms or groups containing silicon atoms from 1 to 10 times and, in the $SiR^7R^8(O_nSiR^9R^{10})_mR^{11}$-radicals, where they function as terminal groups, the substituents $R^7$, $R^8$ and $R^{11}$ may have the meanings defined in (3a).

The compounds according to the invention may be obtained by reacting the α-ketoesters (VI) and (VII):

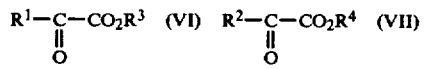

and the corresponding halogen compound in the presence of a substantially equivalent quantity of a base metal in an inert aprotic solvent.

Accordingly, the present invention also provides a process for producing the compounds corresponding to formula (II), characterized in that 0.5 mole of each of the following α-ketoesters (VI and (VII):

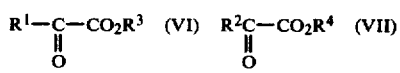

is reacted in the presence of a substantially equivalent quantity of a base metal with from 0.4 to 1.2 moles, preferably from 0.5 to 1.1 moles, of an organohalogen compound (VIII) or (IX):

$$R^5X \qquad (VIII)$$

$$R^6X \qquad (IX)$$

in which X represents chlorine, bromine or iodine and $R^5$ and $R^6$ are as defined in (2) above, or with from 0.4 to 1.2 moles, preferably from 0.5 to 1.1 moles, of a monochloro-organosilane, disilane or polysilane, disiloxane or polysiloxane corresponding to the following formula (X):

$$ClSiR^7R^8(O_nSiR^9R^{10})_mR^{11} \qquad (X)$$

or with from 0.3 to 0.8 mole, preferably from 0.4 to 0.6 mole of a dichloro-organosilane, disilane or polysilane, disiloxane or polysiloxane corresponding to the following formula (XI):

$$Cl_2SiR^7(O_nSiR^9R^{10})_mR^{11} \qquad (XI)$$

or with from 0.2 to 0.6 mole, preferably from 0.2 to 0.4 mole, of a trichloro-organosilane, disilane or polysilane, disiloxane or polysiloxane corresponding to the following formula (XII):

$$Cl_3Si(O_nSiR^9R^{10})_mR^{11} \qquad (XII)$$

in which the substituents in formulae (X) to (XII) are each as defined in (3a) above and the indices are as defined above, or with from 0.1 to 0.7 mole, preferably from 0.2 to 0.5 mole, of tetrachlorosilane, in an inert aprotic solvent until the exothermic reaction is over, the resulting reaction product is hydrolysed, the organic phase is separated off and the solvent is distilled off.

The present invention also relates to the use of the compounds of formula (II) according to the invention as initiators for radically initiatable polymerization reactions.

In the context of the invention, "base metals" are metals which are capable of forming the dianions (XIII):

from the α-ketoesters (VI) and (VII); they are preferably members of the First Main Group, Second Main and Subsidiary Group and Third Main Group of the Periodic System (U. Hofmann and W. Rudorff, Anorganische Chemie, 16th Edition, Friedr. Vieweg & Sohn, Braunschweig, 1966, page 150). Typical representatives of base metals suitable for use in the process according to the invention are lithium, sodium, magnesium, calcium, zinc and aluminium.

The expression "substantially equivalent quantitites" of a base metal means that approximately 1 mole of a monovalent metal, approximately 0.5 mole of a divalent metal or approximately ⅓ mole of a trivalent metal is used per mole of the α-ketoester (VI) or (VII).

The compounds VI and VII may be identical, i.e. $R^1 = R^2$ and $R^3 = R^4$.

In general, the reaction may be carried out at temperatures of from −10° to +70° C. and preferably at temperatures of from −5° to +50° C., if necessary with cooling.

The solvent is generally distilled off at temperatures of from 0° to 120° C. and preferably at temperatures of from 20° to 60° C. under a pressure of from 1 to 760 and preferably from 10 to 200 Torr.

The compounds (II) according to the invention produced from ketoesters, base metals and chloro-silanes, -disilanes, or -polysilanes, -disiloxanes or -polysiloxanes may have a molecular weight, determined as a number average, of from 500 to 6000 and preferably from 800 to 4000.

The molecular weight of the silyl ethers (II) according to the invention is determined by vapour pressure osmometry up to a molecular weight of 3000 and by membrane osmometry for molecular weights above 3000, in each case using acetone as a solvent. The molecular weights of the individual fractions of the reaction mixtures according to the invention may be determined by gel chromatography (using standard substances).

The reaction mixtures obtained during production, which in case (3) contain oligomers of different molecular weight, are normally directly used as polymerization initiators, i.e. they do not have to be separated into the pure substances.

The combinations listed in the following Table represent preferred examples of the base metals, α-ketoesters and organohalogen compounds of chloro-silanes, di- or poly-sil(ox)anes which may be used in accordance with the invention:

TABLE 1

| Initiator | Base metal | α-ketocarboxylic acid ester | Halogen Compound |
|---|---|---|---|
| 1. | magnesium | phenylglyoxylic acid methyl ester | metal iodide |
| 2. | magnesium | phenylglyoxylic acid methyl ester | isopropyl bromide |
| 3. | lithium | phenylglyoxylic acid methyl ester | benzyl chloride |
| 4. | lithium | phenylglyoxylic | cyclohexyl |

TABLE 1-continued

| Initiator | Base metal | α-ketocarboxylic acid ester | Halogen Compound |
|---|---|---|---|
| 5. | magnesium | acid methyl ester<br>t-butyl glyoxylic acid ethyl ester | bromide<br>benzyl chloride |
| 6. | magnesium | pyruvic acid ethyl ester | hexyl bromide |
| 7. | magnesium | phenylglyoxylic acid methyl ester | chlorotrimethyl silane |
| 8. | magnesium | phenylglyoxylic acid methyl ester | dichlorodimethyl silane |
| 9. | magnesium | phenylglyoxylic acid methyl ester | trichloromethyl silane |
| 10. | magnesium | phenylglyoxylic acid methyl ester | tetrachlorosilane |
| 11. | lithium | phenylglyoxylic acid methyl ester | diphenyl dichloro silane |
| 12. | lithium | phenylglyoxylic acid hexyl ester | dichlorodimethyl silane |
| 13. | calcium | phenylglyoxylic acid hexyl ester | trichloromethyl silane |
| 14. | magnesium | 4-methylphenyl glyoxylic acid methyl ester | trichloromethyl silane |
| 15. | magnesium | 4-chlorophenyl glyoxylic acid hexyl ester | dichlorodimethyl silane |
| 16. | magnesium | phenylglyoxylic acid lauryl ester | chlorotriethyl silane |
| 17. | aluminium | 4-biphenylyl glyoxylic acid ethyl ester | tetrachlorosilane |
| 18. | sodium | phenylglyoxylic acid methyl ester | chlorotrimethyl silane |
| 19. | magnesium | pyruvic acid ethyl ester | chlorotrimethyl silane |
| 20. | magnesium | pyruvic acid ethyl ester | tetrachlorosilane |
| 21. | magnesium | t-butyl glyoxylic acid hexyl ester | chlorotriethyl silane |
| 22. | magnesium | t-butyl glyoxylic acid hexyl ester | trichloromethyl silane |
| 23. | magnesium | cyclohexyl glyoxylic acid hexyl ester | chlorotrimethyl silane |
| 24. | magnesium | sec-butyl glyoxylic acid hexyl ester | trichloromethyl silane |
| 25. | magnesium | n-hexyl glyoxylic acid methyl ester | chlorotrimethyl silane |
| 26. | magnesium | isopropyl glyoxylic acid benzyl ester | dichlorodiphenyl silane |
| 27. | magnesium | phenyl glyoxylic acid-(octaethylene glycol)-ester | trichloromethyl silane |
| 28. | magnesium | phenyl glyoxylic acid-(trimethyol propane)-ester, etherified with 4 moles of ethylene oxide | trichloromethyl silane |

Preferred inert aprotic solvents are aromatic and alkyl aromatic compounds, such as benzene and toluene; ethers such as diethyl ether, diisopropyl ether, dibutyl ether, anisole, tetrahydrofuran, dioxane or 1,2-dimethoxy ethane; trialkyl phosphates such as triethyl phosphate or tributyl phosphate; N,N-disubstituted amides such as dimethyl formamide, N,N'-dimethyl acetamide and phosphoric acid-tris-(dimethyl amide). Other suitable inert aprotic solvents are described in "Methoden der Organischen Chemie" (Houben-Weyl), Vol. XIII/2a, pages 59–70, Georgh Thieme-Verlag, Stuttgart, 1973. Solvents which have proved to be particularly suitable consist of from 0 to 80 parts by weight of benzene or toluene, from 1 to 100 parts by weight of tetrahydrofuran of from 0 to 50 parts by weight of triethyl phosphate or phosphoric acid-tris-(dimethyl amide). In order not unnecessarily to dilute the reaction mixture, as little solvent as possible is generally used. In most cases, a ratio by weight of ketoester to solvent of 1:2 is entirely adequate.

It is advisable to bear in mind that partial decomposition is actually possible under the reaction conditions. If, therefore, the compounds (II) according to the invention should show low reactivity attributable to decomposition of the compounds used as initiators during production, the reaction temperature will be reduced.

The dissociation temperature of the compounds (II) according to the invention may be determined by a simple colour reaction. This is because the radicals which are formed during thermal decomposition are capable of declouring quinoid dyes. To carry out the test, a small quantity of quinoid dye, for example methylene blue, thionine or neutral red, is dissolved in a solvent which is free from molecular oxygen, for example glycol or xylene, and an at least equivalent quantity of the compound (II) according to the invention is added to the resulting solution. The temperature at which the dye is decoloured is the dissociation temperature of the initiator.

The dissociation temperature is governed to a large extent by the structure of the compounds (II). Initiators containing space-filling radicals $R^1$ and $R^2$ (for example aryl or t-butyl) are distinguished by a relatively low dissociation temperature. Initiators in which the substituents $R^1$ and $R^2$ represent primary or secondary alkyl or aralkyl groups only decompose into radicals at relatively high temperatures. In addition, however, the other substituents are also of importance so far as the tendency of the compounds (II) according to the invention towards dissociation is concerned.

In contrast to peroxides, the compounds or mixtures according to the invention decompose without giving off any heat. In addition, in the presence of peroxides, the products according to the invention do not lead to induced decomposition of the peroxide. Accordingly, they are also suitable for subsequently tempering cold-hardened mouldings of unsaturated polyester resins and for desensitizing peroxidic initiators.

Compounds whose polymerization may be initiated by the compounds (II) according to the invention include any radically polymerizable compounds or mixtures thereof, i.e. for example olefins, such as ethylene; conjugated dienes, such as butadiene, isoprene or chloroprene; vinyl chloride; vinylidene chloride; aromatic vinyl compounds, such as styrene or divinyl benzene; vinyl esters, particularly vinyl acetate and vinyl propionate; vinyl ethers, such as vinyl propyl ether or vinyl isobutyl ether; acrylic acid and methacrylic acid and derivatives thereof, such as esters, particularly with aliphatic alcohols containing from 1 to 5 carbon atoms, nitriles, amides, etc.; di(vinylphenyl)-carbonates: diallyl phthalate, diallyl carbonate, diallyl furmarate: di(allylphenyl)carbonates; polyol poly(meth)acrylates; and N,N'-methylene-bis-(methy)acrylamide.

Particularly preferred substances to the polymerized are unsaturated polyester resins, i.e. solutions of α,β-ethylenically unsaturated polyesters in monomers co-polymerizable therewith. Investigation of the unsaturated polyester resins thermally hardened with the compounds (II) according to the invention surprisingly shows that the residual styrene contents are lower than where comparable known initiators of the dibenzyl type are used.

Preferred α,β-ethylenically unsaturated polyesters are the usual polycondensation products of at least one α,β-ethylenically unsaturated dicarboxylic acid generally containing 4 or 5 carbon atoms or ester-forming derivatives thereof, for example anhydrides, optionally in admixture with up to 200 mole percent, based on the unsaturated acid components, of at least one aliphatic saturated $C_4$-$C_{10}$ or cycloaliphatic or aromatic $C_8$-$C_{10}$ dicarboxylic acid or ester-forming derivatives thereof, with at least one polyhydroxy compound particularly dihydroxy compound, containing from 2 to 8 carbon atoms, i.e. polyesters of the type described in the book by J. Bjorksten et al entitled "Polyesters and their Applications," Rheinhold Publishing Corp., New York, 1956.

Examples of preferred unsaturated dicarboxylic acids or their derivatives are maleic acid or maleic acid anhydride and fumaric acid. However, it is also possible to use for example mesaconic acid, citraconic acid, itaconic acid or chloromaleic acid. Examples of the aliphatic saturated and cycloaliphatic or aromatic dicarboxylic acids or their derivatives which may be used in accordance with the invention are phthalic acid or its phthalic acid anhydride, isophthalic acid, terephthalic acid, hexahydro or tetrahydrophthalic acid or their anhydrides, endomethylene tetrahydrophthalic acid or its anhydride, succinic acid or succinic acid anhydride and succinic acid esters and chlorides, adipic acid and sebacic acid. In order to produce flame-resistant resins, it is possible to use for example hexachloroendomethylene tetrahydrophthalic acid, tetrachlorophthalic acid or tetrabromophthalic acid. Suitable dihydric alcohols include ethylene glycol, 1,2-propane diol, 1,3-propane diol, diethylene glycol, dipropylene glycol, 1,3-butane diol, 1,4-butane diol, neopentyl glycol, 1,6-hexane diol, 2,2-bis-(4-hydroxy cyclohexyl)-propane, bis-alkoxylated bisphenol A, perhydro bisphenol and others. It is preferred to use ethylene glycol, 1,2-propane diol, diethylene glycol and dipropylene glycol.

Further modifications are possible through the incorporation of monohydric, trihydric and tetrahydric alcohols containing from 1 to 6 carbon atoms, such as methanol, ethanol, butanol, allyl alcohol, benzyl alcohol, cyclohexanol and tetrahydrofurfuryl alcohol, trimethylol propane, glycerol and pentaerythritol, by the incorporation of mono-, di- and tri-allyl ethers and benzyl ethers of trihydric and higher alcohols containing from 3 to 6 carbon atoms according to German Auslegeschrift No. 1,024,654 and by the incorporation of monobasic acids, such as benzoic acid, or long-chain unsaturated fatty acids, such as oleic acid, linseed oil fatty acid and ricinene fatty acid.

The polyesters have acid numbers of generally from 1 to 100 and preferably from 20 to 70, OH numbers of from 10 to 150 and preferably from 20 to 100 and molecular weights $\overline{M}_n$, determined as number averages, of from about 500 to 5000 and preferably from about 1000 to 3000 (as measured by vapour pressure osmometry in dioxane and acetone; in the case of differing values, the lower value is regarded as the correct value).

Suitable vinyl and vinylidene compounds copolymerizable with the unsaturated polyesters are the unsaturated compounds commonly encountered in polyester technology which preferably contain α-substituted vinyl groups or β-substituted allyl groups, preferably styrene. However, it is also possible for example to use nucleus-chlorinated and nucleus-alkylated or -alkenylated styrenes, in which case the alkyl groups may contain from 1 to 4 carbon atoms, for example vinyl toluene, divinyl benzene, α-methyl styrene, t-butyl styrene or chlorostryrenes; vinyl esters of carboxylic acids containing from 2 to 6 carbon atoms, preferably vinyl acetate; vinyl pyridine, vinyl naphthalene, vinyl cyclohexane, acrylic acid and methacrylic acid and/or their esters (preferably vinyl, allyl and methallyl esters) containing from 1 to 4 carbon atoms in the alcohol component, their amides and nitriles, maleic acid anhydrides, semiesters and diesters containing from 1 to 4 carbon atoms in the alcohol component, semiamides and diamides or cyclic imides, such as N-methyl maleic imide or N-cyclohexyl maleic imide; allyl compounds, such as allyl benzene, and allyl esters, such as allyl acetate, phthalic acid diallyl ester, isophthalic acid diallyl ester, fumaric acid diallyl ester, allyl carbonates, diallyl carbonates, triallyl phosphate and triallyl cyanurate.

Some of the compounds (II) according to the invention are active even at temperatures above 400° C. Complete and rapid hardening is generally obtained with from 0.2 to 1% by weight and preferably with from 0.05 to 0.8% by weight of the compounds (II) according to the invention, based on the substance to be polymerized.

The polymerization reaction is started by heating a mixture of the substance to be polymerized and the compounds (II) according to the invention above a particular starting temperature which may readily be determined in each individual case. Radically polymerizable systems are generally hardened at temperatures of from 60° to 200° C.

Hardening may be carried out in a single operation, although if desired it may even be carried out in stages (cf. British Pat. No. 1,041,641).

The invention is illustrated by the following Examples in which the parts quoted represent parts by weight and the percentages are by weight.

EXAMPLE 1

0.1 g of $HgCl_2$, 12.2 g of magnesium chips and 20 g of phenyl glyoxylic acid methyl ester are introduced into a solvent mixture of 100 g of toluene and 500 g of tetrahydrofuran. A mixture of 144 g of phenyl glyoxylic acid methyl ester and 125 g of isopropyl bromide is then slowly added dropwise at a temperature of from +5° to +30° C. After a short time, the highly exothermic reaction begins and the magnesium dissolves as more of the isopropyl bromide-containing solution is added. On completion of the reaction, the reaction mixture is stirred for 5 hours at 30° C., cooled to +5° C., carefully hydrolysed with 200 ml of water and acidified with 10 ml of 18% hydrochloric acid. The organic phase is diluted with 300 ml of toluene, subsequently separated off and washed three times with water. Removal of the solvent by distillation leaves 150 g of a residue of which, according to analysis by NMR spectroscopy, approximately 25 mole percent consists of 1,2-diphenyl-1,2-diisopropoxy succinic acid dimethyl ester, approximately 45 mole percent of 1,2-diphenyl-1-hydroxy-2-isopropoxy succinic acid dimethyl ester and 30 mole percent of 1,2-diphenyl tartaric acid dimethyl ester.

EXAMPLE 2

The procedure was as in Example 1, except that methyl iodide (140 g) was added instead od the isopropyl bromide. Yield: 148 g, of which approximately 30 mole percent consists of 1,2-diphenyl-1,2-dimethoxy succinic acid dimethyl ester, 40 mole percent of 1,2-diphenyl-1-hydroxy-2-methoxy succinic acid dimethyl ester and 30 mole percent of 1,2-diphenyl tartaric acid dimethyl ester.

EXAMPLE 3

The procedure was as in Example 1, except that all the phenyl glyoxylic acid methyl ester was initially introduced and trimethyl chlorosilane (115 g) was added dropwise instead of the isopropyl bromide. Yield: 160 g, Si-content: 6.2% Composition (as determined by NMR-spectroscopy):

- 35 mole percent of 1,2-diphenyl-1,2-bis-(trimethyl siloxy)-succinic acid dimethyl ester,
- 35 mole percent of 1,2-diphenyl-1-hydroxy-2-trimethyl siloxy succinic acid dimethyl ester,
- 30 mole percent of 1,2-diphenyl tartaric acid dimethyl ester.

EXAMPLE 4

24.3 g of magnesium and 328 g of phenyl glyoxylic acid methyl ester are initially introduced into a solvent mixture of 500 g of toluene, 100 g of phosphoric acid tris-(dimethyl amide) and 50 g of tetrahydrofuran, 15 g of trichloromethyl silane are added at a temperature of from 15° to 30° C. After the reaction has started (exothermic reaction), another 95 g of trichloromethyl silane are added dropwise at 25° to 35° C. The magnesium dissolves completely. On completion of the reaction, the solution is stirred for 4 hours at 30° C., cooled to just 5° C. and hydrolyzed with 600 ml of water. During hydrolysis the temperature should not exceed +20° C. After stirring for another 2 hours at 30° C., the organic phase is separated off, washed three times with 400 ml of water and concentrated in a water jet vacuum at 30° C., leaving as residue a highly viscous liquid which quickly hardens to form a wax-like solid.

Gel chromatography was carried out with a low-molecular-separating column combination filled with Styragel in different pore widths (Waters measuring technique); tetrahydrofuran was used as eluent. Calibration was carried out with phenyl glyoxylic acid methyl ester. Correlated therewith, the following molecular weight distribution is obtained:

| Component | Molecular weight | Percentage area |
| --- | --- | --- |
| 1 | 164 | 2.2 |
| 2 | 330 | 3.0 |
| 3 | 400 | 4.6 |
| 4 | 480 | 2.4 |
| 5 | 700 | 12.0 |
| 6 | 800 | 14.8 |
| 7 | 1240 | 34.6 |
| 8 | 1900 | 20.3 |
| 9 | 2200 | 6.1 |

EXAMPLE 5

The procedure is as in Example 4, except that t-butyl glyoxylic acid hexyl ester (428 g) is used instead of the phenyl glyoxylic acid methyl ester. Working up leaves an oily product which, according to gel chromatography, has the following molecular weight distribution:

| Component | Molecular weight | Percentage area |
| --- | --- | --- |
| 1 | 154 | 5.5 |

-continued

| Component | Molecular weight | Percentage area |
| --- | --- | --- |
| 2 | 310 | 4.2 |
| 3 | 380 | 2.7 |
| 4 | 700 | 14.4 |
| 5 | 840 | 16.0 |
| 6 | 1200 | 24.8 |
| 7 | 1840 | 14.0 |
| 8 | 2320 | 13.7 |
| 9 | 3000 | 4.7 |

EXAMPLE 6

6 g of sodium in filament form are introduced under pressure into a solvent mixture of 250 ml of absolute tetrahydrofuran and 50 ml of triethyl phosphate. A solution of 68 g of 4-chlorophenyl glyoxylic acid hexyl ester and 18 g of dichlorodimethyl silane in 50 ml of absolute tetrahydrofuran is then added dropwise at −5° to 10° C. When all the sodium has dissolved, the mixture is stirred for 3 hours and then hydrolyzed with 300 g of ice. After repeated washing with iced water, the organic phase is concentrated in a water jet vacuum at 15° C.

Removal of the solvent by distillation leaves 101 g of a liquid residue, of which approximately 35% by weight consists of triethyl phosphate.

EXAMPLE 7

An unsaturated polyester, produced from 11 parts of phthalic acid anhydride, 47 parts of maleic acid anhydride and 42 parts of 1,2-propylene glycol at 200° C. (acid number 20, OH-number 30, viscosity at 23° C.: 1500 cP), is dissolved to form a 66% solution in styrene and stabilized with 0.01 part of hydroquinone. 1 part of compound (II) (cf. pages 10,11) of benzpinacol is dissolved in 100 parts of this unsaturated polyester resin.

1 hour after addition of the initiator, 20 g of a resin mixture are introduced into a 16 mm diameter test tube. An iron/constantan thermocouple connected to a temperature-time recorder is immersed to a depth of 3 cm in the resin and, after the measureing apparatus has been switched on, the test tube which is filled to a level of 8 cm is placed in a boiling water bath. The hardening time $t_H$ (time taken to reach the peak temperature minus the time taken to pass the 65° C. line) and the peak temperature ($T_m$) are determined in accordance with DIN 16 945.

The residual styrene contents were iodometrically analysed by the process described by B. Alt in Kunststoffe 52, 133 (1962).

| Initiator | $t_H$(min.) | $T_m$(°C.) | Residual styrene content (%) |
| --- | --- | --- | --- |
| 1 | 5.2 | 230 | 0.35 |
| 5 | 9.8 | 215 | 0.32 |
| 7 | 4.8 | 230 | 0.28 |
| 9 | 4.8 | 230 | 0.30 |
| 14 | 4.9 | 230 | 0.30 |
| 21 | 8.7 | 210 | 0.45 |
| 23 | 10.4 | 190 | 0.60 |
| benzpinacol | 11.0 | 205 | 0.70 |

(COMPARISON TEST)

EXAMPLE 8

The procedure was as in Example 7, except that an oil bath thermostatically regulated to 140° C. was used as the heating bath.

| Initiator | t/(min.) | T_m(°C.) |
|---|---|---|
| 6 | 14.5 | 210 |
| 19 | 13.0 | 225 |
| 23 | 5.0 | 250 |
| 24 | 8.2 | 240 |

EXAMPLE 9

0.2 g of a compound (II) according to the invention is added to 150 g of a 40% solution of styrene in 1,2-dichloroethane.

Each sample is boiled under reflux for 4 hours, followed by the addition of 0.5 ml of a 1% solution of benzoquinone in ethyl acetate. The product is then concentrated in a rotary evaporator at a bath temperature of 35° C. The bath temperature is slowly increased to 60° C. at 14 Torr and then kept for 4 hours at 95° C. Any residual monomers still present are removed by tempering the polymer in a vacuum drying cabinet at 140° C. until it is constant in weight. The polystyrene left as residue is weighed out.

The following initiators of the examples given in Table 1 were investigated:

| Initiator | Polystyrene | Conversion (% of the theoretical) |
|---|---|---|
| — | 0.2 | 0.3 |
| 2 | 14.1 | 23 |
| 5 | 7.0 | 12 |
| 7 | 16.4 | 27 |
| 9 | 13.2 | 22 |
| 15 | 14.4 | 24 |
| 21 | 6.9 | 12 |
| 26 | 3.2 | 5 |

EXAMPLE 10

A 2000 ml stirrer-equipped autoclave was filled with 1 liter of heptane and 1 g of compound (II) (initiators 12 and 16, see Table 1). The solution was purged with nitrogen, after which 430 g of ethylene were introduced under pressure at room temperature. The autoclave was slowly heated to 130° C. The internal pressure initially rose to 450 bars, but fell back to 300 and 280 bars over a period of 60 minutes. The autoclave was then left for 2 hours at 130° C., cooled and vented. After the reactor had been opened, the ethylene polymer was removed with the heptane solution, filtered, washed and dried at 50° C. until constant in weight.

In the case of initiator 12, 180 g of polymer melting at 110° to 113° C. were obtained. In the case of initiator 16, 164 g of polymer melting at 110° to 114° C. were obtained.

We claim:

1. Ethers of 1,2-disubstituted tartaric acid esters corresponding to the following formula (II):

in which

R$^1$ and R$^2$ represent linear or branched C$_1$–C$_{10}$ alkyl radicals optionally substituted by methoxy, chlorine or fluorine, C$_5$–C$_7$ cycloalkyl radicals optionally substituted by C$_1$–C$_4$ alkyl, methoxy, chlorine or fluorine, C$_7$–C$_{10}$ aralkyl radicals optionally substituted by C$_1$–C$_4$ alkyl, methoxy, chlorine or fluorine, or C$_6$–C$_{12}$ aryl radicals optionally substituted by C$_1$–C$_4$ alkyl, methoxy, chlorine or fluorine, R$^3$ and R$^4$ represent linear or branched C$_1$–C$_{18}$ alkyl radicals optionally substituted by methoxy, Chlorine or fluorine, C$_5$–C$_7$ cycloalkyl radicals optionally substituted by C$_1$C$_4$ alkyl, methoxy, chlorine or fluorine, C$_7$–C$_{10}$ aralkyl radicals optionally substituted by C$_1$–C$_4$ alkyl, methoxy, chlorine or fluorine, C$_6$–C$_{10}$ aryl radicals optionally substituted by C$_1$–C$_4$ alkyl, methoxy, chlorine or fluorine, or triorganosilyl radicals containing from 3 to 18 carbon atoms, R$^5$ and R$^6$ represent (1) a hydrogen atom with the proviso that at most one of the two substituents is a hydrogen atom, (2) C$_1$–C$_{10}$ alkyl radicals optionally substituted by methoxy, chlorine or fluorine, C$_5$–C$_7$ cycloalkyl radicals optionally substituted by C$_1$–C$_4$ alkyl, methoxy, chlorine or fluorine, C$_7$–C$_{10}$ aralkyl radicals optionally substituted by C$_1$–C$_4$ alkyl, methoxy, chlorine or fluorine, or (3) SiR$^7$R$^8$ (O$_n$SiR$^9$R$^{10}$)$_m$R$^{11}$ and R$^7$, R$^8$ and R$^{11}$ represent (a) methyl, ethyl, phenyl, benzyl, chloromethyl, hydroxyl, methoxy or ethoxy, or (b) a radical corresponding to the formula (III) or (IV):

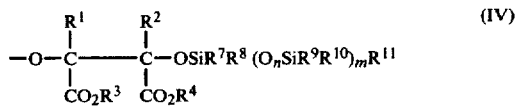

R$^9$ and R$^{10}$ are as defined in (3a) and n=0 or 1, m=0 or an integer or from 1 to 10; and in which the compounds corresponding to formula (II) in case (3) may contain the component structure (V):

attached through silicon atoms or groups containing silicon atoms from 1 to 10 times and, in the SiR$^7$R$^8$ (O$_n$SiR$^9$R$^{10}$)$_m$R$^{11}$-radicals where they function as terminal groups, the substituents R$^7$, R$^8$ and R$^{11}$ may have the meanings defined in (3a).

2. A process for producing the ethers claimed in claim 1, characterized in that 0.5 mole of each of the following α-ketoesters (VI) and (VII):

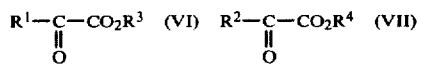

is reacted in the presence of a substantially equivalent quantity of a base metal with from 0.4 to 1.2 moles, preferably from 0.5 to 1.1 moles, of an organohalogen compound (VIII) or (IX):

$$R^5X \quad \text{(VIII)}$$

$$R^6X \quad \text{(IX)}$$

in which X represents chlorine, bromine or iodine and $R^5$ and $R^6$ are as defined in (2) above,
or with
from 0.4 to 1.2 moles, preferably from 0.5 to 1.1 moles, of a monochloro-organosilane, disilane or polysilane, disiloxane or polysiloxane corresponding to the following formula (X):

$$ClSiR^7R^8(O_nSiR^9R^{10})_mR^{11} \quad \text{(X)}$$

or with
from 0.3 to 0.8 mole, preferably from 0.4 to 0.6 mole, of a dichloro-organosilane, disilane or polysilane, disiloxane or polysiloxane corresponding to the following formula (XI):

$$Cl_2SiR^7(O_nSiR^9R^{10})_mR^{11} \quad \text{(XI)}$$

or with
from 0.2 to 0.6 mole, preferably from 0.2 to 0.4 mole, of a trichloro-organosilane, disilane or polysilane, disiloxane or polysiloxane corresponding to the following formula (XII):

$$Cl_3Si(O_nSiR^9R^{10})_mR^{11} \quad \text{(XII)}$$

the substituents in formulae (X)–(XII) each having the meaning defined in (3a) above and the indices being as defined above, or with from 0.1 to 0.7 mole, preferably from 0.2 to 0.5 mole, of tetrachlorosilane, in an inert aprotic solvent until the exothermic reaction is over, the resulting reaction product is hydrolyzed, the organic phase is separated off and the solvent is distilled off.

* * * * *